(12) United States Patent
Yamaura

(10) Patent No.: US 8,445,600 B2
(45) Date of Patent: May 21, 2013

(54) CROSSLINKING AGENT, AND CROSSLINKING POLYMER COMPOSITION AND MOLDED PRODUCT FORMED OF THE SAME

(75) Inventor: Mabuko Yamaura, Fukushima-ken (JP)

(73) Assignee: Nippon Kasei Chemical Company Limited, Iwaki-shi, Fukushima-ken (JP)

( * ) Notice: Subject to any disclaimer, the term of this patent is extended or adjusted under 35 U.S.C. 154(b) by 181 days.

(21) Appl. No.: 12/991,970

(22) PCT Filed: May 11, 2009

(86) PCT No.: PCT/JP2009/002046
§ 371 (c)(1),
(2), (4) Date: Jan. 13, 2011

(87) PCT Pub. No.: WO2009/139141
PCT Pub. Date: Nov. 19, 2009

(65) Prior Publication Data
US 2011/0105687 A1    May 5, 2011

(30) Foreign Application Priority Data
May 12, 2008  (JP) ................. 2008-124847

(51) Int. Cl.
C08C 19/22 (2006.01)
C08F 8/06 (2006.01)
C08F 8/30 (2006.01)
C07D 251/04 (2006.01)

(52) U.S. Cl.
USPC ............ 525/375; 525/326.3; 525/326.5; 525/329.1; 525/329.9; 525/331.1; 525/391; 525/418; 525/467; 544/221

(58) Field of Classification Search
USPC .............. 544/221; 525/375, 326.3, 326.5, 525/329.1, 329.9, 331.1, 391, 418, 467; 521/902
See application file for complete search history.

(56) References Cited

U.S. PATENT DOCUMENTS
6,610,778 B2 *  8/2003  Takita et al. ................ 524/588

FOREIGN PATENT DOCUMENTS
| JP | 5-295043 | 11/1993 |
| JP | 05-295043 | 11/1993 |
| JP | 11-279162 | 10/1999 |
| JP | 2002-371069 | 12/2002 |
| JP | 2004-203948 | 7/2004 |

OTHER PUBLICATIONS

Extended European Search Report in EP 09 74 6348 dated Jul. 17, 2012.
Comments from German Associate dated Aug. 20, 2012.
Aronovich et al, "Properties of heat-resistant cyanoacrylate adhesives . . . ", Klei, Germetiki, Tekhnologii, vol. 5, Jan. 25, 2008; pp. 12-14, XP009160828, p. 13; example IX; table 3.
Fattakhov et al, "1-alkyl 3,5-diallylisocyanurates . . . ", Russian Journal of General Chemistry, Nauka/Interperiodica, MO, vol. 74, No. 8, Aug. 1, 2004, pp. 1267-1276, XP019300807; ISSN: 1608-3350, table 3.
Mmokrousov et al, "Properties of thermally stable anaerobic compositions", Plasticheskie Massy, vol. 12, 1989, pp. 33-35, XP009160830, p. 34; examples 1-2, table 1.
Gavrilyuk, "Modification of the surface of polyformaldehyde fibers" Khimicheskaya Tekhnologiya (Kiev), vol. 3, 1985, pp. 24-26, XP009160825, p. 25; table 1, and Database Registry [online] Chemical Abstracts Service, Columbus, Ohio, Nov. 16, 1984, database accession No. 54887-34-2 rn 54887-34-2.
Fainerman et al, "Evaluation of the effectiveness of potential finishing agents-lubricants", Plasticheskie Massy, vol. 9, 1973, pp. 38-40, XP009160829, p. 38; examples 10, 11, 13; table 1.
Fedorenko et al, "Synthesis of allyl derivatives of s-triazine", Sintez I Fiziko-Khimiya Polimerov, vol. 10, 1972, pp. 15-18, XP009160822, p. 15-p. 17; examples.
Khomenkova et al, "Polymerization of alkyl diallyl isocyanurates", Sintez I Fiziko-Khimiya Polimerov, vol. 9, 1971, pp. 30-33, XP009160821, whole document.
Balitskaya et al, "Synthesis of 5-alkyl-1,3-diallyl isocyanurates with functional groups in the alkyl residue", Zhurnal Organicheskoi Khimii, vol. 2, No. 8, 1966, pp. 1421-1423, XP009160820, p. 421.
International Search Report for PCT/JP2009/002046, mailed Jul. 14, 2009.

* cited by examiner

Primary Examiner — Fred M Teskin
(74) Attorney, Agent, or Firm — Nixon & Vanderhye P.C.

(57) ABSTRACT

The present invention provides a crosslinking agent which is excellent in processing characteristics and crosslinking performance, and is capable of preventing staining of a molded product upon molding in a metal mold which tends to be induced when using the crosslinking agent together with a triallyl isocyanurate. The crosslinking agent of the present invention comprises an isocyanurate derivative represented by the following general formula (I):

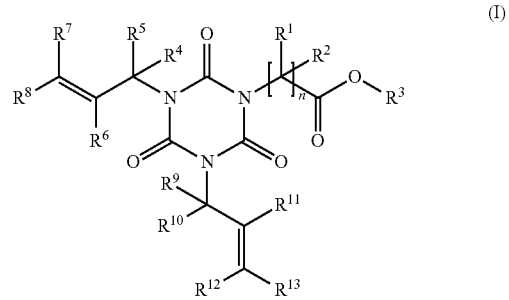

wherein $R^1$ and $R^2$ are each independently a hydrogen atom, a methyl group or an ethyl group; $R^4$ to $R^{13}$ are each independently a hydrogen atom or a methyl group; $R^3$ is a hydrocarbon group having 1 to 3 carbon atoms which may have a substituent group; and n is an integer of 1 or 2.

14 Claims, No Drawings

CROSSLINKING AGENT, AND CROSSLINKING POLYMER COMPOSITION AND MOLDED PRODUCT FORMED OF THE SAME

This application is the U.S. national phase of International Application No. PCT/JP2009/002046, filed 11 May 2009, which claims priority to Japanese Application No. 2008-124847, filed 12 May 2008, the entire contents of each of which are hereby incorporated by reference.

TECHNICAL FIELD

The present invention relates to a crosslinking agent, and a crosslinking composition and a molded product formed of the composition.

BACKGROUND ART

It is known that isocyanurate derivatives are effective as a crosslinking agent for crosslinking polymers such as crosslinking elastomers and crosslinking thermoplastic resins (Patent Documents 1 and 2). In particular, among these isocyanurate derivatives, triallyl isocyanurates (hereinafter referred to merely as "TAIC") are excellent in not only heat resistance but also chemical resistance.

However, TAIC which is in the form of a viscous liquid at an ordinary temperature tends to suffer from problems such as poor processing characteristics upon kneading, etc. For example, when kneading the TAIC with a crosslinking elastomer such as a nitrile rubber and a fluororubber using an open roll mill, there tends to arise such a problem that the kneaded material tends to suffer from roll slippage owing to sags and runs of the TAIC. In particular, when kneading the TAIC with the fluororubber having a poor compatibility with the TAIC, the roll slippage tends to be caused more remarkable, resulting in poor workability.

Also, when kneading the TAIC with the crosslinking thermoplastic resin such as polyamides and polyesters using a twin-screw extruder, it may be difficult to not only uniformly blend these components with each other but also supply the components to the extruder, resulting need of using a special supply apparatus therefor.

In particular, when kneading TAIC with the fluororubber in the applications such as semiconductors in which no filler such as carbon is incorporated into the fluororubber, it may be very difficult to supply the TAIC thereto, so that the addition time is prolonged, and the amount of the TAIC added must be limited owing to non-uniformity of the TAIC-added fluororubber, thereby causing considerable deterioration in crosslinking performance thereof. In addition, when molding the TAIC-compounded elastomer composition in a metal mold, there tend to arise problems such as contamination of the metal mold and staining of the resulting molded product (final product) owing to bleeding-out of the liquid TAIC on the surface of the molded product during the crosslinking step. Incidentally, the TAIC may be subjected to the kneading step and the crosslinking step which are carried out in separate stages from each other, in some cases. In such cases, the resulting crosslinking polymer composition in the form of a kneaded material is subjected to crosslinking reaction, for example, after preserving the composition for several days, and then formed into the final product. Under such a condition, bleeding-out of the liquid TAIC tends to be induced even during the preservation, so that the problems such as contamination of the metal mold and staining of the molded product tend to become still more remarkable.

The above conventional problems concerning the processing characteristics are one of the reasons for causing significant influences on productivity or crosslinking performance when subjecting the crosslinking elastomer or crosslinking thermoplastic resin to crosslinking reaction.

Patent Document 1: Japanese Patent Application Laid-Open (KOKAI) No. 2003-2992

Patent Document 2: Japanese Patent Application Laid-Open (KOKAI) No. 2005-238477

DISCLOSURE OF THE INVENTION

Problems to be Solved by the Invention

The present invention has been accomplished to solve the above conventional problems. An object of the present invention is to provide a crosslinking agent which is excellent in processing characteristics and crosslinking performance. Another object of the present invention is to provide a crosslinking agent which is free from contamination of a metal mold or staining of a molded product even when molding a crosslinking polymer composition obtained by kneading the crosslinking agent therewith not only immediately after the kneading but also after the composition is preserved for an appropriate period of time after the kneading.

Means for Solving Problems

That is, in a first aspect of the present invention, there is provided a crosslinking agent comprising an isocyanurate derivative represented by the following general formula (I).

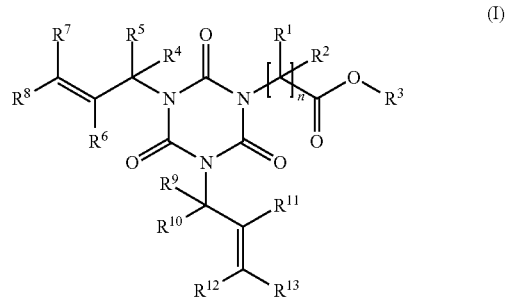

(wherein $R^1$ and $R^2$ are each independently a hydrogen atom, a methyl group or an ethyl group; $R^4$ to $R^{13}$ are each independently a hydrogen atom or a methyl group; $R^3$ is a hydrocarbon group having 1 to 3 carbon atoms which may have a substituent group; and n is an integer of 1 or 2).

In a second aspect of the present invention, there is provided a crosslinking polymer composition comprising the above crosslinking agent and a crosslinking polymer. Also, in a third aspect of the present invention, there is provided a molded product produced by molding the above crosslinking polymer composition.

EFFECT OF THE INVENTION

The crosslinking agent of the present invention can exhibit excellent processing characteristics while maintaining a good crosslinking performance which is inherent to the conventionally used TAIC. More specifically, the crosslinking agent of the present invention is kept in the form of a crystal at an ordinary temperature and is therefore free from sags and runs or roll slippage upon subjected to kneading treatment unlike the TAIC kept in the form of a liquid at an ordinary temperature. In addition, in particular, when kneading the TAIC with a fluororubber under such a condition that no filler is added thereto, the resulting crosslinked fluororubber can exhibit a uniform transparency owing to an excellent dispersibility of the TAIC therein. Further, the crosslinking agent of the present invention is capable of preventing staining of a molded product upon molding in a metal mold which tends to be induced by using the TAIC.

PREFERRED EMBODIMENTS FOR CARRYING OUT THE INVENTION

The present invention is described in detail below.

First, the crosslinking agent of the present invention is explained. The crosslinking agent of the present invention comprises an isocyanurate derivative represented by the following general formula (I).

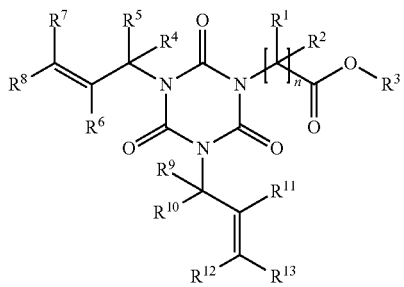

(wherein $R^1$ and $R^2$ are each independently a hydrogen atom, a methyl group or an ethyl group; $R^4$ to $R^{13}$ are each independently a hydrogen atom or a methyl group; $R^3$ is a hydrocarbon group having 1 to 3 carbon atoms which may have a substituent group; and n is an integer of 1 or 2).

Specific examples of $R^3$ in the general formula (I) include a methyl group, an ethyl group, an n-propyl group and an isopropyl group.

The isocyanurate derivative represented by the general formula (I) may be produced, for example, by reacting an isocyanuric acid derivative represented by the following general formula (II) and a halide derivative represented by the following general formula (III) with each other in an aprotic polar solvent in the presence of a base.

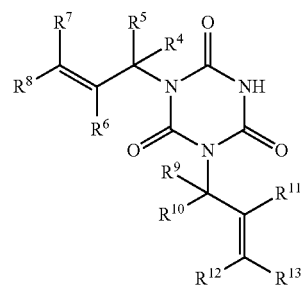

(wherein $R^4$ to $R^{13}$ are each independently a hydrogen atom or a methyl group).

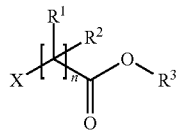

(wherein $R^1$ and $R^2$ are each independently a hydrogen atom or a methyl group; $R^3$ is a hydrocarbon group having 1 to 3 carbon atoms; X is a halogen atom; and n is an integer of 1 or 2).

Specific examples of the isocyanuric acid derivative represented by the general formula (II) include diallyl isocyanurate, dimethallyl isocyanurate and monoallyl monomethallyl isocyanurate. Specific examples of the halide derivative represented by the general formula (III) include methyl bromoacetate, ethyl bromoacetate, ethyl chloroacetate, isopropyl bromoacetate, methyl bromoproionate and ethyl bromovalerate.

Examples of the aprotic polar solvent include N,N-dimethyl formamide (DMF), N,N-dimethyl acetamide and dimethyl sulfoxide (DMSO). Examples of the base include alkali metal carbonates such as potassium carbonate and sodium carbonate, potassium oxide, alkali metal hydroxides such as sodium hydroxide and potassium hydroxide, and tertiary amines such as triethyl amine. The reaction temperature may vary depending upon the kinds of reactant components used, and is usually 20 to 200° C.

In addition, the isocyanurate derivative represented by the general formula (I) may also be produced by reacting the halide derivative represented by the general formula (III) with a (meth)allyl halide and an alkali cyanate.

Specific examples of the isocyanurate derivative represented by the general formula (I) include methoxycarbonyl methyldiallyl isocyanurate, ethoxycarbonyl methyldiallyl isocyanurate, isopropoxycarbonyl methyldiallyl isocyanurate and ethoxycarbonyl methyldimethallyl isocyanurate.

Next, the crosslinking polymer composition of the present invention is explained. The crosslinking polymer composition of the present invention is characterized by comprising the above crosslinking agent and a crosslinking polymer. The crosslinking polymer as used herein means a polymer having a crosslinking performance such as a crosslinking elastomer and a crosslinking thermoplastic resin. In the followings, the crosslinking polymer composition of the present invention is explained with respect to two separate types, i.e., one type using a crosslinking elastomer as the crosslinking polymer (crosslinking elastomer composition) and another type using a crosslinking thermoplastic resin as the crosslinking polymer (crosslinking thermoplastic resin composition).

(Crosslinking elastomer composition)

The crosslinking elastomer used in the crosslinking elastomer composition means an elastomer having active sites which can be crosslinked by generation of radicals. Examples of the crosslinking elastomer include natural rubber, isoprene rubber, butadiene rubber, ethylene propylene rubber, styrene rubber, nitrile rubber, hydrogenated nitrile rubber, chloroprene rubber, chloro-sulfonated polyethylene, acrylic rubber, ethylene acrylic rubber, silicone rubber, fluororubber, hydrin rubber and ethylene-vinyl acetate copolymers. These elastomers may be used in combination of any two or more thereof to form a blended rubber. Among these elastomers, the preferred crosslinking elastomer is a fluororubber.

The amount of the crosslinking agent compounded in the composition is usually 0.5 to 10 parts by weight and preferably 3 to 5 parts by weight based on 100 parts by weight of the crosslinking elastomer.

When the crosslinking elastomer composition of the present invention is subjected to crosslinking reaction by heating, an organic peroxide is usually used as an essential component of the composition. The organic peroxide used in the composition is not particularly limited as long as it can generate a peroxy radical under the vulcanization conditions. Examples of the organic peroxide include di-t-butyl peroxide, dicumyl peroxide, 2,5-dimethyl-2,5-di(benzoylperoxy)hexane, 2,5-dimethyl-2,5-di(t-butylperoxy)hexane, 1,1-bis(t-butylperoxy)-3,5,5-trimethyl cyclohexane, 2,5-dimethylhexane-2,5-dihydroxyperoxide, t-butylcumyl peroxide, $\alpha,\alpha'$-bis(t-butylperoxy)-p-diisopropyl benzene, 2,5-dimethyl-2,5-di(t-butylperoxy)hexyne-3, benzoyl peroxide and t-butylperoxybenzene.

The amount of the organic peroxide compounded in the composition may vary depending upon the kind of crosslinking elastomer used, and is usually 0.1 to 10 parts by weight and preferably 0.5 to 5 parts by weight based on 100 parts by weight of the crosslinking elastomer. Meanwhile, when subjecting the composition to radiation crosslinking, the organic peroxide is not necessarily required.

The additives to be compounded in the composition are not particularly limited. Examples of the suitable additives include a reinforcing material, a filler, a plasticizer, a processing assistant, a lubricant, an anti-ageing agent, a pigment and a coupling agent.

The crosslinking elastomer composition of the present invention can be obtained by mixing the above respective components. The mixing method is not particularly limited, and may be carried out using an ordinary kneader such as a Banbury mixer, a kneader and an open roll mill depending upon the kind of crosslinking elastomer used. In this case, the mixing of the respective components may be carried out with excellent processing characteristics for a short period of time without occurrence of sags and runs of the crosslinking agent and roll slippage.

The crosslinking of the crosslinking elastomer composition is carried out by the method of adding the organic peroxide, etc., to the composition and then heating the composition (heat crosslinking), radiation crosslinking, etc. Among these methods, especially preferred is the heat crosslinking. The heat crosslinking may be carried out, for example, using an injection molding machine, a press molding machine, etc. The heating temperature used in the heat crosslinking is usually 150 to 200° C., and the heating time is usually 2 to 30 min. If necessary, thereafter, the crosslinked composition may be further subjected to secondary crosslinking by heating it at a temperature of about 150 to about 200° C. for about 1 to about 10 hr. Examples of the radiation usable in the radiation crosslinking include accelerated electron beams, X-rays, $\alpha$-rays, $\beta$-rays and $\gamma$-rays. The irradiation dose may vary depending upon the kind of crosslinking elastomer used, etc., and is usually 0.1 to 500 kGy.

(Crosslinking thermoplastic resin composition)

The crosslinking thermoplastic resin used in the crosslinking thermoplastic resin composition means a thermoplastic resin having active sites which can be crosslinked by generation of radicals. Examples of the crosslinking thermoplastic resin include vinyl chloride resins, polyolefin resins, acrylic resins, polystyrene resins, polycarbonate resins, polyester resins, polyamide resins, polyphenylene ether resins, polyacetal resins and fluororesins. Among these crosslinking thermoplastic resins, preferred are polyamide resins and polyester resins, and more preferred are polyamide 6, polyamide 66 and polybutylene terephthalate.

The amount of the crosslinking agent compounded in the composition is usually 0.5 to 25 parts by weight, preferably 1 to 15 parts by weight and more preferably 1 to 10 parts by weight based on 100 parts by weight of the crosslinking thermoplastic resin.

When the crosslinking thermoplastic resin composition of the present invention is subjected to crosslinking reaction by heating, an organic peroxide is usually used as an essential component of the composition. The organic peroxide used in the composition is not particularly limited as long as it can generate a peroxy radical under the crosslinking conditions. Examples of the organic peroxide include dicumyl peroxide, t-butylcumyl peroxide and $\alpha,\alpha'$-bis(t-butylperoxy-m-isopropyl)benzene.

The amount of the organic peroxide compounded in the composition may vary depending upon the crosslinking thermoplastic resin used, and is usually 0.1 to 20 parts by weight based on 100 parts by weight of the crosslinking thermoplastic resin. Meanwhile, when subjecting the composition to radiation crosslinking, addition of the organic peroxide is not necessarily required.

The additives are not particularly limited. Examples of the additives include a polymerization inhibitor, a filler, a pigment, a stabilizer, a lubricant, a releasing agent and a plasticizer.

The crosslinking thermoplastic resin composition of the present invention can be obtained by mixing the above respective components. The mixing method is not particularly limited, and may be carried out using an ordinary kneader such as a twin-screw extruder, a kneader, a Banbury mixer and an open roll mill depending upon the kind of resin used. In this case, the respective components may be uniformly mixed with each other with excellent processing characteristics without occurrence of sags and runs of the crosslinking agent.

The crosslinking thermoplastic resin composition of the present invention may be crosslinked by heat crosslinking, radiation crosslinking, etc., similarly to the crosslinking elastomer composition. The heat-crosslinking may be carried out using an injection molding machine, an extrusion molding machine, a press molding machine, etc. The heating conditions used upon the heat crosslinking may vary depending upon the kind of crosslinking thermoplastic resin used, and are therefore not particularly limited. The heating temperature is usually 50 to 200° C., and the heating time is usually 2 to 30 min. Examples of the radiation used in the radiation crosslinking include accelerated electron beams, X-rays, $\alpha$-rays, $\beta$-rays and $\gamma$-rays. The irradiation dose may vary depending upon the kind of crosslinking thermoplastic resin used, etc., and is usually 1 to 1000 kGy.

The crosslinking polymer composition of the present invention is excellent in processing characteristics while maintaining a good crosslinking performance which is inherent to the conventionally used TAIC, so that it becomes possible to produce a molded product from the composition with a high productivity. Meanwhile, a mixture of the crosslinking elastomer and the crosslinking thermoplastic resin may also be used as the crosslinking polymer.

EXAMPLES

The present invention is described in more detail below by Examples. However, these Examples are only illustrative and not intended to limit the present invention thereto, and the variations and other modifications are possible unless they depart from the scope of the present invention. Meanwhile, the derivatives synthesized were analyzed by the following methods.

(1) Melting point:

The melting point was measured at a temperature rise rate of 1° C./min using "FP62" manufactured by Mettler Toledo Inc.

(2) Purity:

The purity was determined from an area percentage measured by liquid chromatography. The liquid chromatography was carried out in a mixed solvent comprising acetonitrile and water using "LC-10AVP" manufactured by Shimadzu Seisakusho Co., Ltd., and equipped with a column "INERTSIL ODS-3" (25 cm).

(3) Mass spectrometric analysis:

The mass spectrometric analysis was carried out using GC-MS "Auto Mass" manufactured by JEOL, Ltd.

Synthesis Example 1

(Synthesis of ethoxycarbonyl methyldiallyl isocyanurate):

In the presence of 48.1 g (0.23 mol) of diallyl isocyanurate and 34.6 g (0.25 mol) of potassium carbonate, 41.8 g (0.25 mol) of ethyl bromoacetate were reacted in 240.5 g of dimethyl formamide at 50° C. for 2 hr. Thereafter, the obtained reaction mixture was cooled and then filtered to remove inorganic substances therefrom. The resulting filtrate was subjected to distillation under reduced pressure to recover the solvent therefrom. The obtained filtration residue was diluted with chloroform and extracted with an alkali aqueous solution and an acid aqueous solution. The thus obtained extraction solution was washed with water, dried with anhydrous magnesium sulfate and then filtered, and further subjected to distillation under reduced pressure to recover chloroform therefrom. On the other hand, the obtained residue was mixed with isopropyl alcohol to precipitate crystals. Thereafter, the obtained mixture was subjected to filtration to recover a filter cake therefrom. The thus recovered filter cake was dried to obtain 57.7 g (yield: 85%) of ethoxycarbonyl methyldiallyl isocyanurate represented by the following structural formula (A). As a result, it was confirmed that the obtained reaction product had a melting point of 65° C., a purity of 97% and a GC-MS (CI) m/e of 295.

(Structural formula A)

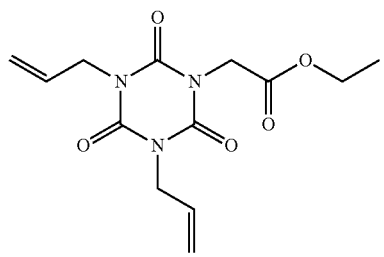

Synthesis Example 2

(Synthesis of methoxycarbonyl methyldiallyl isocyanurate):

In the presence of 33.3 g (0.16 mol) of diallyl isocyanurate and 23.2 g (0.17 mol) of potassium carbonate, 25.6 g (0.17 mol) of methyl bromoacetate were reacted in 175.5 g of dimethyl formamide at 50° C. for 2 hr. Thereafter, the obtained reaction mixture was cooled and then filtered to remove inorganic substances therefrom. The resulting filtrate was subjected to distillation under reduced pressure to recover the solvent therefrom. The obtained filtration residue was subjected to distillation under reduced pressure to obtain 33.4 g (yield: 86%) of methoxycarbonyl methyldiallyl isocyanurate in the form of crystals represented by the following structural formula (B). As a result, it was confirmed that the obtained reaction product had a melting point of 49 to 72° C., a purity of 95% and a GC-MS (CI) m/e of 281.

(Structural formula B)

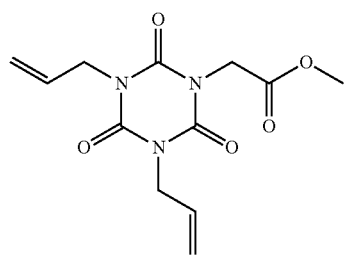

Example 1 and Comparative Example 1:

The isocyanurate derivative obtained in Synthesis Example 1 and TAIC were mixed with each other with the formulation shown in Table 1 and subjected to kneading treatment using an open roll mill. Upon the kneading, the mixture was visually observed to evaluate the processing characteristics of the crosslinking agent such as sags and runs, roll slippage and dispersibility. The resulting elastomer composition was subjected to press vulcanization at 160° C. for 10 min, and then to secondary vulcanization at 180° C. for 4 hr. The other vulcanization conditions such as a metal mold and a pressure were determined according to JIS K6299. The thus obtained respective vulcanized products were evaluated for compression permanent strain characteristics thereof according to JIS K6262. The results are shown in Table 2.

TABLE 1

| Formulation | Example 1: isocyanurate derivative | Comparative Example 1: TAIC[4] |
|---|---|---|
| Fluororubber[1] | 100 | 100 |
| MT carbon[2] | 20 | 20 |
| Perhexa 25B-40[3] | 3.75 | 3.75 |
| Crosslinking agent | 4 | 4 |

Note:
[1]"DAI-EL G-902" produced by Daikin Industries Ltd.
[2]"SURMAX MT N990" produced by Carbons Inc.
[3]2,5-Dimethyl-2,5-di(t-butylperoxy)hexane produced by NOF Co., Ltd.
[4]Triallyl isocyanurate produced by Nippon Kasei Chemical Co., Ltd.

TABLE 2

| Evaluation items | Example 1 | Comparative Example 1 |
|---|---|---|
| Evaluation of crosslinking agent | | |
| Appearance | Powder | Liquid |
| Handling property | ○ | X |
| Sags and runs | ○ | X |
| Roll slippage | ○ | X |
| Dispersibility | ○ | Δ |
| Tensile strength | 15 | 17 |
| 100% Tensile stress | 4.7 | 4.2 |
| Elongation | 350 | 380 |
| Rate of change in tensile strength (250° C. × 70 hr) | −31 | −33 |
| Compression permanent strain (200° C. × 70 hr) | 26 | 23 |

Example 2 and Comparative Example 2:

The isocyanurate derivative obtained in Synthesis Example 2 and TAIC were mixed with each other with the formulation shown in Table 3 and subjected to kneading treatment using an open roll mill. Upon the kneading, the mixture was visually observed to evaluate the processing characteristics of the crosslinking agent such as sags and runs, roll slippage and dispersibility. The resulting elastomer composition was subjected to press vulcanization at 160° C. for 10 min, and then to secondary vulcanization at 180° C. for 4 hr. The other vulcanization conditions such as a metal mold and a pressure were determined according to JIS K6299. The crosslinked product obtained after the secondary vulcanization was transparent and uniform. The thus obtained respective vulcanized products were evaluated for compression permanent strain characteristics thereof according to JIS K6262.

TABLE 3

| Formulation | Example 2: isocyanurate derivative | Comparative Example 2: TAIC[(4)] |
|---|---|---|
| Fluororubber[(1)] | 100 | 100 |
| Perhexa 25B-40[(3)] | 1.1 | 1.1 |
| Crosslinking agent | 5 | 5 |

Note:
[(1)]"DAI-EL G-902" produced by Daikin Industries Ltd.
[(3)]2,5-Dimethyl-2,5-di(t-butylperoxy)hexane produced by NOF Co., Ltd.
[(4)]Triallyl isocyanurate produced by Nippon Kasei Chemical Co., Ltd.

TABLE 4

| Evaluation items | Example 2 | Comparative Example 2 |
|---|---|---|
| Evaluation of crosslinking agent | | |
| Appearance | Powder | Liquid |
| Handling property | ○ | X |
| Sags and runs | ○ | X |
| Roll slippage | ○ | X |
| Dispersibility | ○ | X |
| Tensile strength | 14 | 13 |
| 100% Tensile stress | 4.7 | 4.3 |
| Elongation | 390 | 350 |
| Rate of change in tensile strength | −35 | −15 |

TABLE 4-continued

| Evaluation items | Example 2 | Comparative Example 2 |
|---|---|---|
| Rate of change in elongation at breaking | +13 | +31 |
| Compression permanent strain | 26 | 23 |

Example 3 and Comparative Example 3:

The effect of preventing contamination of the molded product obtained in a metal mold when using the crosslinking agent according to the present invention on was confirmed by the following method.

That is, the same kneading treatment procedure as defined in each of Example 1 and Comparative Example 1 was conducted except that the amount of the crosslinking agent used was changed from 4 parts by weight as shown in the formulation of FIGS. 1 to 9 parts by weight. Next, the resulting kneaded material (crosslinking polymer composition) was separated into two parts. The one part of the composition was immediately subjected to vulcanization treatment, whereas the other part of the composition was preserved at a temperature of 25° C. and a relative humidity of 60% for 10 days and then subjected to vulcanization treatment. The vulcanization treatment was conducted as follows. That is, each part of the composition was subjected to press vulcanization at 180° C. for 10 min using a cylindrical metal mold (having a diameter of 30 mm and a height of 10 mm), and then to secondary vulcanization at 180° C. for 4 hr. The pressure used upon the press vulcanization was 110 kgf/cm². The appearance of the respective molded products obtained after the secondary vulcanization was observed, and those molded products having white spots or white turbidity on the surface thereof were regarded as defectives. Thus, the number of the defectives per 10 products (defective percentage) was examined. The results are shown in Table 5. In Table 5, the "molded product A" represents a molded product obtained by subjecting the crosslinking polymer composition produced by the kneading treatment to vulcanization immediately after the kneading treatment, whereas the "molded product B" represents a molded product obtained by preserving the crosslinking polymer composition produced by the kneading treatment for 10 days and then subjecting the composition to vulcanization.

TABLE 5

| | Example 3 | | Comparative Example 3 | |
|---|---|---|---|---|
| Crosslinking agent | Isocyanurate derivative obtained in Synthesis Example 1 | | TAIC | |
| Defective percentage | Molded product A | Molded product B | Molded product A | Molded product B |
| | 0/10 | 0/10 | 5/10 | 10/10 |

The invention claimed is:

1. A crosslinking polymer composition consisting of a crosslinking agent and a crosslinking polymer, wherein said crosslinking agent comprising an isocyanurate derivative represented by the following general formula (I):

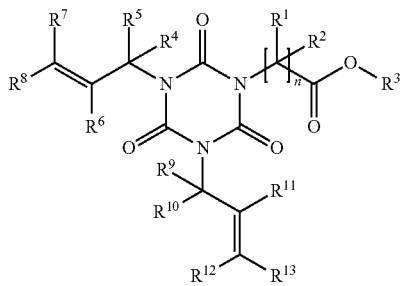 (I)

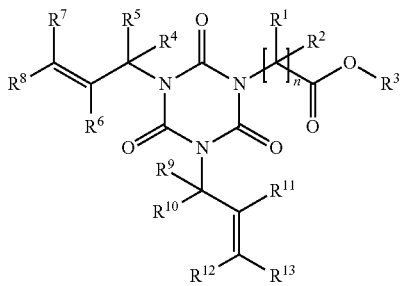 (I)

wherein $R^1$ and $R^2$ are each independently a hydrogen atom, a methyl group or an ethyl group; $R^4$ to $R^{13}$ are each independently a hydrogen atom or a methyl group; $R^3$ is a hydrocarbon group having 1 to 3 carbon atoms optionally containing a substituent; and n is an integer of 1 or 2.

2. A crosslinking polymer composition according to claim 1, wherein the crosslinking polymer is a crosslinking elastomer or a crosslinking thermoplastic resin.

3. A crosslinking polymer composition according to claim 2, wherein the crosslinking elastomer is at least one selected from the group consisting of a natural rubber, isoprene rubber, butadiene rubber, ethylene propylene rubber, styrene rubber, nitrile rubber, hydrogenated nitrile rubber, chloroprene rubber, chloro-sulfonated polyethylene, acrylic rubber, ethylene acrylic rubber, silicone rubber, fluororubber, hydrin rubber and ethylene-vinyl acetate copolymer.

4. A crosslinking polymer composition according to claim 2, wherein the amount of the crosslinking agent compounded in the composition is 0.5 to 10 parts by weight based on 100 parts by weight of the crosslinking elastomer.

5. A crosslinking polymer composition according to claim 2, wherein the crosslinking thermoplastic resin is at least one selected from the group consisting of a vinyl chloride resin, polyolefin resin, acrylic resin, polystyrene resin, polycarbonate resin, polyester resin, polyamide resin, polyphenylene ether resin, polyacetal resin and fluororesin.

6. A crosslinking polymer composition according to claim 5, wherein the amount of the crosslinking agent compounded in the composition is 0.5 to 25 parts by weight, based on 100 parts by weight of the crosslinking thermoplastic resin.

7. A molded product produced by molding the crosslinking polymer composition as defined in claim 1.

8. A crosslinking polymer composition consisting of a crosslinking agent, a crosslinking polymer and an organic peroxide, wherein said crosslinking agent comprising an isocyanurate derivative represented by the following general formula (I):

wherein $R^1$ and $R^2$ are each independently a hydrogen atom, a methyl group or an ethyl group; $R^4$ to $R^{13}$ are each independently a hydrogen atom or a methyl group; $R^3$ is a hydrocarbon group having 1 to 3 carbon atoms optionally including a substituent group; and n is an integer of 1 or 2.

9. A crosslinking polymer composition according to claim 8, wherein the crosslinking polymer is a crosslinking elastomer or a crosslinking thermoplastic resin.

10. A crosslinking polymer composition according to claim 9, wherein the crosslinking elastomer is at least one selected from the group consisting of a natural rubber, isoprene rubber, butadiene rubber, ethylene propylene rubber, styrene rubber, nitrile rubber, hydrogenated nitrile rubber, chloroprene rubber, chloro-sulfonated polyethylene, acrylic rubber, ethylene acrylic rubber, silicone rubber, fluororubber, hydrin rubber and ethylene-vinyl acetate copolymer.

11. A crosslinking polymer composition according to claim 9, wherein the amount of the crosslinking agent compounded in the composition is 0.5 to 10 parts by weight based on 100 parts by weight of the cros slinking elastomer and the amount of the organic peroxide compounded in the composition is 0.1 to 20 parts by weight based on 100 parts by weight of the crosslinking elastomer.

12. A crosslinking polymer composition according to claim 9, wherein the crosslinking thermoplastic resin is at least one selected from the group consisting of a vinyl chloride resin, polyolefin resin, acrylic resin, polystyrene resin, polycarbonate resin, polyester resin, polyamide resin, polyphenylene ether resin, polyacetal resin and fluororesin.

13. A crosslinking polymer composition according to claim 12, wherein the amount of the crosslinking agent compounded in the composition is 0.5 to 25 parts by weight, based on 100 parts by weight of the crosslinking thermoplastic resin and the amount of the organic peroxide compounded in the composition is 0.1 to 20 parts by weight based on 100 parts by weight of the crosslinking thermoplastic resin.

14. A molded product produced by molding the crosslinking polymer composition as defined in claim 8.

* * * * *